(12) United States Patent
Glaser et al.

(10) Patent No.: US 8,103,461 B2
(45) Date of Patent: Jan. 24, 2012

(54) METHOD FOR DETERMINING THE TEMPORAL POSITION OF A WAVE PACKET AND FLOW MEASURING DEVICE

(75) Inventors: Eckard Glaser, Gerbrunn (DE); Daniel Scheder, Wurzburg (DE)

(73) Assignee: Carefusion Germany 234 GmbH, Hochberg (DE)

( * ) Notice: Subject to any disclaimer, the term of this patent is extended or adjusted under 35 U.S.C. 154(b) by 647 days.

(21) Appl. No.: 11/910,562

(22) PCT Filed: Mar. 28, 2006

(86) PCT No.: PCT/DE2006/000544
§ 371 (c)(1),
(2), (4) Date: Feb. 17, 2009

(87) PCT Pub. No.: WO2006/105761
PCT Pub. Date: Oct. 12, 2006

(65) Prior Publication Data
US 2009/0276167 A1 Nov. 5, 2009

(30) Foreign Application Priority Data
Apr. 4, 2005 (DE) .......................... 10 2005 015 456

(51) Int. Cl.
*G01F 1/66* (2006.01)
(52) U.S. Cl. .......................... 702/48; 73/861.28; 702/45
(58) Field of Classification Search .................. 702/45, 702/48, 100, 103, 106; 73/24.01, 628, 861.27, 73/861.28; 600/438, 529, 532
See application file for complete search history.

(56) References Cited

U.S. PATENT DOCUMENTS

| 5,419,326 | A | 5/1995 | Harnoncourt |
| 5,509,414 | A | 4/1996 | Hoek |
| 5,777,237 | A * | 7/1998 | Collier et al. .............. 73/861.28 |
| 6,261,238 | B1 | 7/2001 | Gavriely |
| 6,279,379 | B1 | 8/2001 | Logue et al. |
| 6,305,233 | B1 * | 10/2001 | Braathen et al. ........... 73/861.28 |
| 2002/0143479 | A1 | 10/2002 | Fukuhara |
| 2003/0018276 | A1 | 1/2003 | Mansy et al. |
| 2004/0093957 | A1 | 5/2004 | Buess et al. |

FOREIGN PATENT DOCUMENTS

| CH | 669463 | 3/1989 |
| DE | 10206134 | 8/2002 |
| EP | 051293 | 5/1982 |
| EP | 0243515 | 11/1987 |
| EP | 0597060 | 5/1994 |
| EP | 0713080 | 5/1996 |

(Continued)

Primary Examiner — John H Le
(74) Attorney, Agent, or Firm — King & Schickli, PLLC

(57) ABSTRACT

The invention relates to a method for determining the temporal position of a wave packet (31) in a flow measuring apparatus, and to a flow measuring apparatus. The method includes the sampling of the wave packet at a plurality of points in time, wherein a measured value is created at each point in time. Subsequently, a sum of products (43, 54, 55, 63, 64) is calculated, wherein each product is calculated for a determined point in time from a plurality of points in time and each product is the product of a value of a compare function (44, 53, 56, 61, 62) at the determined point in time and the measured value at the determined point in time. Finally, the temporal position of the wave packet is calculated from the sum of products.

22 Claims, 10 Drawing Sheets

FOREIGN PATENT DOCUMENTS

| | | |
|---|---|---|
| EP | 0 797 105 | 9/1997 |
| EP | 1279368 | 1/2003 |
| GB | 2 275 108 | 8/1994 |
| WO | 9005283 | 5/1990 |
| WO | 9831989 | 7/1998 |
| WO | 0026618 | 5/2000 |

* cited by examiner

METHOD FOR DETERMINING THE TEMPORAL POSITION OF A WAVE PACKET AND FLOW MEASURING DEVICE

BACKGROUND OF THE INVENTION

The invention relates to the processing of signals for the exact measurement of a propagation time difference. The invention also relates to flow measuring apparatus, in particular to flow measuring apparatus for detecting the airflow during inspiration and expiration, which utilize the capture effect of ultrasound. Such flow measuring apparatus are also referred to as spirometers.

A number of apparatus are known, which utilize the capture effect of sound waves in fluids, especially air. There are substantially two construction types, which are illustrated in FIGS. 11 and 12.

The flow measuring apparatus 1 illustrated in FIG. 11 comprises a tube 2 as well as a first ultrasonic transducer 4 and a second ultrasonic transducer 5. The tube has a diameter d and an axis 3. Both ultrasonic transducers 4 and 5 are disposed on a second axis 6 so that each of the two transducers picks up the ultrasound generated by the respective other transducer. The second axis 6 encloses with axis 3 of the tube an angle $\alpha$. If the medium in tube 2 is at rest, the sound propagation times $t_{45}$ and $t_{54}$ from ultrasonic transducer 5 to ultrasonic transducer 5 and from ultrasonic transducer 5 to ultrasonic transducer 4, respectively, are defined by $$t_{45} = t_{54} = \frac{L}{c} \quad (1)$$

with L designating the distance between both ultrasonic transducers and c the sound velocity in the medium at rest.

A flow in the tube 2 toward the right shortens the sound propagation time $t_{45}$ from ultrasonic transducer 4 to ultrasonic transducer 5. At the same time, the sound propagation time $t_{54}$ from ultrasonic transducer 5 to ultrasonic transducer 4 is extended. A rectangular flow profile is defined by $$t_{45} = \frac{L}{c + v \cdot \cos(\alpha)} \quad (2)$$

$$t_{54} = \frac{L}{c - v \cdot \cos(\alpha)} \quad (3)$$

with v designating the velocity of the fluid toward the right. By introducing the propagation time difference $\Delta t$ and the mean propagation time $t_0$ $$\Delta t \equiv t_{54} - t_{45} \quad (4)$$

$$t_0 \equiv \frac{t_{54} + t_{45}}{2} \quad (5)$$

one obtains for the flow velocity v:

$$v = \frac{c}{2\cos(\alpha)} \frac{\Delta t}{t_0} \quad (6)$$

The sound velocity in the medium at rest can be calculated from (2) and (3):

$$c = \frac{L}{t_0 - \frac{1}{4}\frac{\Delta t^2}{t_0}} \quad (7)$$

By inserting formula (7) into (6) one obtains:

$$\dot{V} = C_1 \frac{L}{2\cos(\alpha)} \frac{\Delta t}{t_0^2 - \frac{1}{4}\Delta t^2} \quad (8)$$

The constant $C_1$ is here the conversion factor between the flow velocity v and the flow rate $\dot{V}$. The constant $C_1$ substantially includes the cross-sectional surface of tube 2, wherein r designates the radius of tube 2.

$$C_1 = C_2 \pi r^2 \quad (9)$$

The constant $C_2$ stands for a rectangular flow profile 1. In reality a velocity profile is formed in the tube, so that the velocity of the fluid depends on the position within the tube, on the flow rate and on the viscosity of the fluid. With respect to typical flow rates, the medium air and a tube diameter of two to three centimeters a laminar or turbulent flow range is formed at the wall of the tube and a turbulent flow range in the center of the tube. The greater the flow rate, the smaller is the laminar range and the greater is the turbulent range. This flow profile is responsible for non-linearities in the characteristic of the sensor.

The flow in the tube can be calculated from the propagation times $t_{45}$ and $t_{54}$ or from the propagation time difference $\Delta t$ and the mean propagation time $t_0$. This measuring principle is described, inter alia, in EP 0 051 293 A1, EP 0 243 515 A1, EP 0 597 060 B1, CH 669 463 A5, WO 00/26618 A1 and EP 0 713 080 A1. The smaller the angle $\alpha$, the greater is the propagation time difference at the same flow.

The prior flow measuring apparatus 11 illustrated in FIG. 12 includes a U-shaped tube, which is comprised of a horizontal leg 12 and two vertical legs 17 and 18. The flow measuring apparatus 11 moreover includes ultrasonic transducers 14 and 15 disposed on an axis 13. The axis 13 is, at the same time, the axis of the horizontal leg 12. This structure has the advantage that the flow direction extends parallel to the axis of both ultrasonic transducers, thereby turning the angle $\alpha$ to 0° and, thus, to $\cos(\alpha)=1$. A disadvantage is the complicated construction as well as eddies which occur in the transition range between the vertical and the horizontal legs. Such a type of construction is described, for example, in WO 90/05283 A1 or EP 1 279 368 A2.

Irrespective of the constructional types it is known (e.g. WO 90/05283, EP 1 279 368 A2) to provide the ultrasonic transducers with acoustic impedance converters so as to improve the sound transmission between the fluid and the ultrasonic transducer and vice versa.

The state and the composition of the gas to be measured varies during the respiration. The ambient conditions are referred to as Ambient Temperature Pressure (ATP), which can be converted to Body Temperature Pressure Saturated (BTPS). Exhaled gas has a temperature of about 34° C. to 37° C. and is completely saturated with water vapor, that is, it corresponds to BTPS.

Additionally known is the sing-around technique, for example, from EP 0 713 080 A1. In the sing-around technique sound pulses are repeatedly transmitted from one ultrasonic transducer to the other ultrasonic transducer. As soon as a pulse is received, the next pulse is transmitted. After 1 to 200 pulses the direction is reversed. In this method, the resolution per time unit of the sound propagation time is increased at the expense of the measuring rate. This is particularly significant if media with a high sound velocity are concerned, in particular liquids, or if the propagation time can only be determined by involving, for technical reasons, intensive noise.

To analyze especially functions or signals that vary with time, for example, the correlation analysis, the Fourier analysis or transformation, the short-time Fourier transformation and the wavelet transformation are known.

The correlation coefficient φ of two functions f(t) and g(t) depending on time t and being defined at an interval of $T_1$ to $T_2$, is defined as:

$$\varphi = \frac{\int_{T_1}^{T_2} f(t)g(t)dt}{\sqrt{\int_{T_1}^{T_2} f^2(t)dt \int_{T_1}^{T_2} g^2(t)dt}} \quad (10)$$

The correlation coefficient may be interpreted as a quantity for the similarity of two functions.

Moreover, the cross-correlation function φ (KKF) is defined as time average of the internal product of the two functions f(t) and g(t) shifted against each other by the time T:

$$\Phi(\tau) = \frac{1}{T_2 - T_1} \int_{T_1}^{T_2} f(t)g(t+\tau)dt \quad (11)$$

By Fourier transformation, periodical functions with the period $(T_2-T_1)$ can entirely be represented as weighted sum of sine and cosine functions. The Fourier coefficients can be comprehended as correlation factor of a periodic function and the base vectors of the Fourier space.

The Fourier transformation is predestinated to provide global information about a signal f(t) because its base functions extend over the entire time domain and do not allow any temporal locating ability.

To analyze transient or time-limited signals, the short-time Fourier transformation (STFT) was developed, which corresponds to a development from a one-dimensional time function into the two-dimensional time-frequency level. The signal is here divided into ranges which are assumed to be quasi-stationary, which are subjected to a windowed Fourier transformation independently of each other (Jürgen Niederholz, *Anwendungen der Wavelet-Transformation in Übertragungssystemen*, University of Duisburg, 1999 (http://www.ub.uni-duisburg.de/diss/diss0016/inhalt.htm). The window function in the time domain likewise causes a windowing in the frequency domain so that the STFT has a constant effective bandwidth Δω over the total frequency domain and an effective temporal expansion Δt over the total time domain.

The constant effective bandwidth and the restriction to sine and cosine functions were still perceived as a limitation under the STFT. Both restrictions are removed under the wavelet transformation. A general introduction into the wavelet transformation is given by Antje Ohihoff, *Anwendung der Wavelettransformation in der Signalverarbeitung*, University of Bremen, 1996. The function ψ(t) represents a valid wavelet if a real, finite constant $C_\psi$ exists, wherein $\tilde{\Psi}(\omega)$ is the Fourier transform of functions ψ(t).

$$C_\Psi = \int_{-\infty}^{\infty} \frac{|\tilde{\Psi}(\omega)|^2}{\omega} d\omega \quad (12)$$

One essential idea of the wavelet transformation consists in skillfully choosing the function ψ(t) and in adapting it to the problem to be solved, so that the functions to be analyzed can be described with a small number of wavelets. In other words, only a small number of coefficients of the base functions is to considerably differ from 0.

Based on a base wavelet or mother wavelet the remaining base functions, which form a complete basis for the function space, are generated with a translation parameter b and a dilatation parameter a according to equation (13).

$$\Psi_{a,b}(t) = \frac{1}{\sqrt{|a|}} \Psi\left(\frac{t-b}{a}\right); a, b \in \mathcal{R}, a \neq 0 \quad (13)$$

By equation (13) the so-called quality $Q=\omega_M/\Delta\omega$ over the frequency domain is kept constant which, in the context of wavelet transformation, is also called scaling range. $\omega_M$ is here a center frequency. In nature many phenomena occur, the quality of which is constant.

SUMMARY OF THE INVENTION

It is the object of the invention to allow the use of less expensive components and/or to increase the accuracy of the propagation time measurement by means of an intelligent evaluation method.

This object is achieved with the teaching of the independent claims.

Preferred embodiments of the invention are subject matters of the dependent claims.

An advantage of using a weighted sum of measured values of a wave packet for determining the temporal position of the wave packet is that, by this, a great portion of the energy of the wave packet is evaluated, so that the temporal uncertainty becomes small and the temporal position can be determined very exactly.

Advantageously, a compare function is used for the weighting, which resembles the shape of the wave packet. A sine and cosine function resembles at least a period or a few periods of the ultrasound packet.

The use of a sine and a cosine function as compare functions is advantageous because the position of the wave packet within a period can thus be determined with the aid of an arc tangent function, without the calculation of other compare functions.

The use of an exponential envelope, which is similar to a bell-shaped curve, fits the total shape of the compare function to the shape of a wave packet. Thus, it is possible to evaluate practically the total energy of the wave packet and to determine the temporal position with an optimum accuracy.

The iterative calculation of the temporal position of a wave packet reduces the number of the necessary calculations of product sums and can, thus, save calculation time.

In order to verify whether the temporal position of the wave packet is not shifted by one or more periods, the compare functions can be shifted by one or more periods and product sums can be calculated at these points.

For this purpose, also the geometrical sum of two sum products can be calculated, which involves an even smaller calculation expenditure. It is also possible, for the same purpose, to directly compare the measured values with fractions of maximums and/or minimums.

A maximum search in product sums of measured values by means of a compare function shifted by a different distance makes it possible to keep the program code short.

A square interpolation by means of a parabola is well suited for the search of the maximum. Besides, the curve of a parabola in the proximity of the vertex coincides well with the curve of a sine or cosine function at a maximum because the second order Taylor expansion is here sufficient.

BRIEF DESCRIPTION OF THE FIGURES

Preferred embodiments of the invention shall be explained in more detail below, with reference to the accompanying drawings. In the drawings.

DETAILED DESCRIPTION

As can be seen from the above formulae, in particular formula (8), especially the propagation time difference $\Delta t$ and the mean propagation time $t_0$ must be measured as exactly as possible. The other quantities entering the flow rate $\dot{V}$, i.e. $C_1$, $C_2$, L, $\alpha$, and/or r, are largely constant and can be determined either directly or by means of calibration measurements. Also the non-linearities, which entail that $C_1$ and $C_2$ depend on $\dot{V}$ and, thus, on $\Delta t$, can be gotten under control by standard measurements and the fitting of model curves, e.g. polynomials, to the measured values.

Thus, there remains the technical problem to measure the propagation time difference $\Delta t$ or the propagation times $t_{45}$ and $t_{54}$ with sufficient exactness. This problem is equivalent to the determination of the temporal position of ultrasound packets, which define, after all, the beginning and the end of $\Delta t$. In the embodiments described herein, ultrasonic transducers SC.131.XLV (SECO Sensor Consult GmbH) are employed. A typical center frequency of 310 kHz, a typical bandwidth (±3 dB) of ±40 kHz and a sonic cone width of 11° (−3 dB) are specified for these ultrasonic transducers. Ultrasound having the frequency $f_{US}$=312.5 kHz is used, because it is advantageous, though not necessary, if the sampling rate $f_s$ is an integer multiple of the ultrasonic frequency $f_{US}$. Under normal conditions ultrasound is practically not subjected to any dispersion. To achieve the aimed at exactness of the flow measurement the temporal position of an ultrasound packet must be determined approximately to the nanosecond. The sampling of the signal provided by an ultrasonic transducer at a sampling rate of one gigahertz and the subsequent searching for the maximum in the samples involves great cost. Yet, this embodiment is deemed to be an embodiment according to the invention.

It has shown that the algorithms described below already provide for the demanded temporal exactness of 1 ns at sampling rates $f_s$=5 MHz. At present, sampling rates up to 25 MHz can be achieved with moderate technical and financial expenditures.

Figure 5:
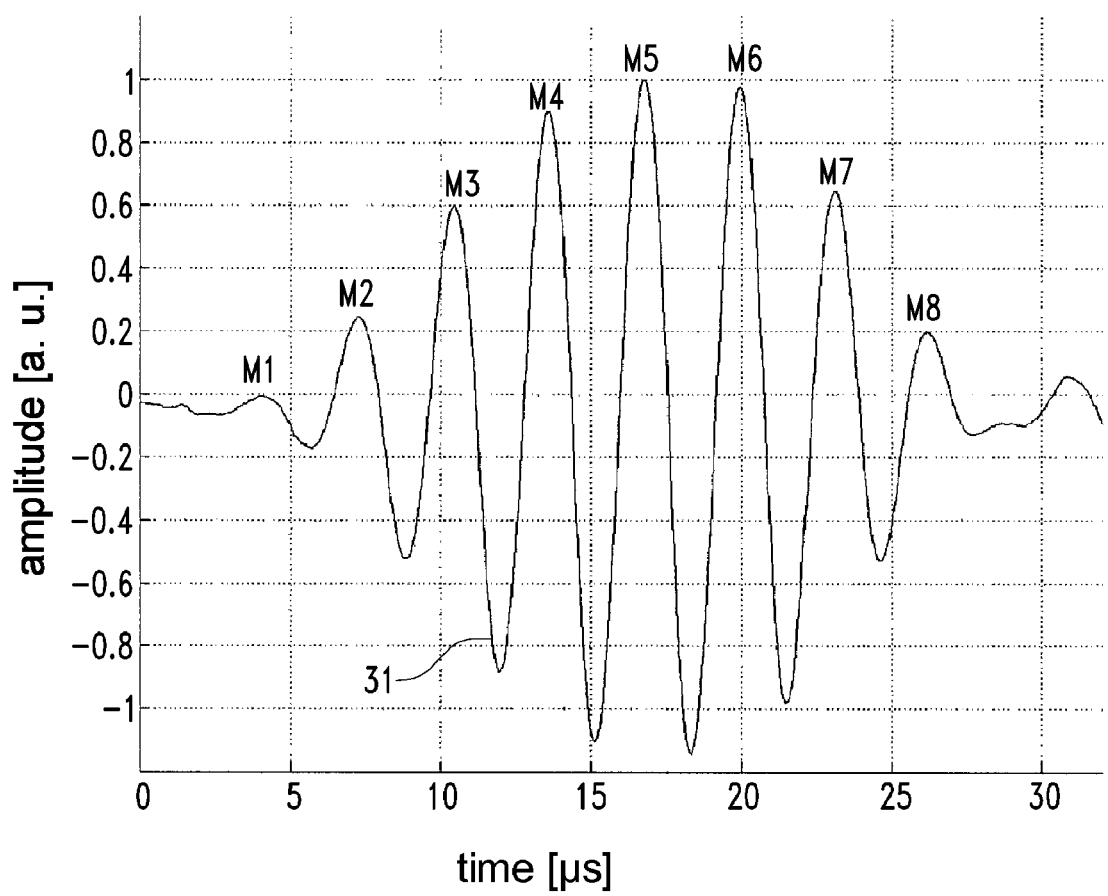
FIG. 5 shows a typical, received ultrasound packet when using the TiDO, TriTraX or WaveTraX algorithm.

The signal provided by the analog-digital converter 94 or 95 includes measured values $W_j$ which have a time interval of $1/f_s$. A typical ultrasound packet is shown in FIG. 5. The local maximums are numbered with M1 to M8. M5 marks the global maximum.

The measured values $W_j$ are noisy and show an unknown offset. Therefore, the search for local maximums or zeros without a preceding signal processing does not provide any usable results, even if the sampling rate would be sufficiently high.

TIDO Algorithm

The Time Domain Only (TiDO) algorithm is substantially based on a determination of the phase position of a single oscillation period in the wave packet. The oscillation with the greatest amplitude has most of the energy and, thus, the greatest signal-to-noise ratio (SNR), wherein the additive noise is assumed to be constant over the total wave packet. The propagation time is determined in multiple steps.

1. In the first step 41 the absolute maximum $M=W_{JM}$ is determined at point $j_M$.

The first step is performed only if, for example, no preceding measured value $T_{M,previous}$ is available after the apparatus is switched on. If a preceding measured value is available, step 41 can be replaced by step 48, which is described below.

The maximum variation of the propagation times $t_{45}$ and $t_{54}$ to be expected is in the range of ±20 µs, wherein the propagation times come to approximately 160 µs. Including the length of the ultrasound packet of approximately 30 µs, thus, approximately 70 µs*$f_S$ data points $W_i$ have to be analyzed in step 41.

By taking into account the periodicity of the sound packet the search algorithm in step 41 may be optimized, so that not all measuring points have to be verified. One starts with an estimated value for the point of the global maximum $j_M$. Similar to step 48, this may be the maximum $T_{M,previous}$ determined in the preceding measurement or also any optional point after the apparatus was switched on. M is initialized with $W\,T_{M,previous}$. One verifies the point $j_{M+1}$ on the right thereof. If $W_{jM}<W_{jM+1}$, one proceeds in this direction until $W_{jE}<M*0.99$, whereby the new maximum M is stored. If now $W_{jM}>0.99M$, one also verifies the other direction toward the left until $W_{jA}<0.99M$. If there is a new maximum, it is stored in M. By this, one obtains as interim result a local maximum $M=W_{jM}$. In the worst case slightly more than S/2 points have been compared until now. One now verifies $W_{jM-nS}$ und $W_{jM+nS}$, n=1, 2, . . . . The maximum of these values is a sufficiently good estimate for the absolute maximum. Because of the bell-shaped envelope the estimate does not necessarily represent the maximum, and it can be expected that the estimate is the worse the higher n is.

2. The data points $W_j$ in the interval $$j \in [j_M - S/2; j_M + S/2[ \tag{14}$$

now correspond to the oscillation period with the greatest amplitude, which is "cut out" by means of a rectangular window function in step 42 for the further signal processing. S is here the number of the measured values in an oscillation period of the ultrasound packet, wherein $$S = f_S/f_{US} \tag{15}$$

For a sampling frequency $f_S$ of 5 MHz and $f_{US}$ of 312.5 kHz S has a value of 16.

3. Now, the time-discrete cyclic variant $Y_\tau$ of the cross-correlation function is calculated in step 43.

$$Y_\tau = \sum_{i=j_M-S/2}^{j_M+S/2-1} W_i f_{i,\tau} \quad (16)$$

$$f_i = \cos\left(\frac{2\pi f_{US} i}{f_S}\right), -\pi \leq \frac{2\pi f_{US} i}{f_S} < \pi \quad (17)$$

The calculation of equation (17) is accomplished in step 44. The values $f_i$ can be calculated offline, for example, during the compilation or assembly, and can be stored in a field which is also called a lookup table. The values $f_i$ relating to the propagation time are read out from this field. When using formulae (16) and (17), approximately two periods of the cosine have to be stored in the lookup table. By explicitly returning to the base period according to equation (17a) the lookup table can be limited to one period.

$$f_{i,\tau} = \begin{cases} f_{i+\tau} & \forall \ i+\tau \leq S \\ f_{i+\tau-S} & \forall \ i+\tau > S \end{cases} \quad (17a)$$

4. In $Y_\tau$ the maximum is now searched for at point $T_M$ in step 45. It can be expected that $T_M \approx j_M$. A slight offset can be a result of noise in the measuring points $W_j$. The step size of $Y_\tau$ corresponds to that of $W_j$ and, thus, to $1/f_S$. Hence, it does not yet satisfy the required exactness of 1 ns.

5. One possibility for the more exact determination of the maximum is to lay a parabola $P_\tau$ according to formula (18) through the maximum $Y_{\tau M}$ and the two neighboring points $Y_{\tau M-1}$ and $Y_{\tau M-1}$ in step 46, and to determine the position of the vertex $\tau_{Max}$ according to formula (19) in step 47.

$$P_\tau = aY_\tau^2 + bY_\tau + c \quad (18)$$

$$\tau_{Max} = -\frac{b}{2a} = \frac{1}{2f_S} \frac{Y_{\tau M+1} - Y_{\tau M-1}}{Y_{\tau M-1} + Y_{\tau M+1} - 2Y_{\tau M}} \quad (19)$$

The temporal position of the ultrasound packet now results from equation (20):

$$t = \frac{\tau_{Max}}{f_S} \quad (20)$$

The TiDO algorithm would already provide for a sufficient exactness. It is necessary, however, to analyze plenty of data points for the first step 41, because it must be ensured that, even if the change rate of the sound propagation time is at a maximum, especially due to a change in the flow velocity v of the medium, the interval chosen in step 42 is included in the measuring points to be analyzed. Therefore, step 48 is introduced additionally.

6. The maximum $T_{M,previous}$ determined in the preceding measurement is assumed (step 48), in the subsequent measurement, to be the maximum $j_M$ which was found in the first step 41, so that the maximum search in step 41 becomes redundant. It is not significant that the maximum $M=W_{jM}$ is located in the center of the interval chosen in step 42. Also the two neighboring periods do not contain much less energy than the period including the maximum.

It is important, however, that the maximum is located in the interval chosen in step 42. This is the case if the phase between two repetitions of steps 42 to 49 does not change by more than half a period. Since measuring rates of 1 kHz were obtained in case of the prototype and a maximum measuring rate of 6.25 kHz can be derived from the propagation times of approximately 160 µs, this is not a real limitation.

However, these reflections only apply to small flows in which eddy zones are sufficiently small. With a diameter of the tube of about 2 cm velocities of 65 m/s or 240 km/h are reached at the upper measuring limit of 20 l/s. In case of high flows it was observed that the propagation time between two successive measurements varies so strongly that the reference point—i.e. $j_M$ when using the TiDO algorithm or j93 when using the TriTraX algorithm—differs between two successive measurements by more than one ultrasonic period ≈3 µs. This appears to be a result of eddies. These eddies, together with the signal drift, result in an amplitude of the receive signal which is smaller by 20 dB, with a flow of 20 l/s.

Because of the variation of the propagation time with high flows it may be sensible to compare in step 45 the maximum $Y_{TM}$ with the adjacent maximums $Y_{TM\pm nS}$, n=1, 2, ... or $W_{TM}$ with $W_{TM\pm nS}$. Should it be found that $Y_{TM\pm nS}$ and $W_{TM\pm nS}$, respectively, is the absolute maximum, steps 42 to 45 with $T_M \pm nS$ as estimate for $j_M$ should be repeated.

Because of the variation of the propagation time with high flows it may moreover be sensible in all embodiments described in this document to average the propagation times from several successive measurements. The number of the averaged measurements can increase with the flow.

It is disadvantageous that, due to the temperature behavior and the flow dependency of the directional characteristic of the ultrasonic transducers, the waveform of the ultrasound packet shown in FIG. 5 can change. Therefore, due to noise and the small height difference of 1% between the maximums M5 and M6, the maximum M6 can become the absolute maximum. In the event of strong turbulences M4 or M7 may even increase to the global maximum. Therefore, the TiDO algorithm proves to be not so robust and practicable.

Furthermore it is disadvantageous that the maximums of the fitted cosine function $f_i$ and the parabola $P_\tau$ are even more apart the smaller the sampling rate $f_S$ is.

TriTraX Algorithm

These two problems are to be solved by the Trigonometric Transform by Cross (X) Correlation (TriTraX) algorithm. Therefore, a point in the wave packet is used, which identifies the oscillation period within the ultrasound packet more reliably. In FIG. 5, the height difference between the maximums M4 and M5 is about 14% of the height of M5 and is reliably detectable.

1. In the first step 51, again, the absolute maximum $M=W_{jM}$ of the ultrasound packet is searched for.

Because of the variation of the propagation time with high flows it may be sensible to compare, in step 51, the maximum $W_{jM}$ with the adjacent maximums $W_{TM\pm nS}$, n=1, 2, .... Should it be found that $W_{TM\pm nS}$ is the absolute maximum, jM=jM±nS is set.

2. Now, point $j_{93}$ is determined, the ordinate value of which $W_{j93}$ is closest to 0.93*M or exceeds this value in a wave packet for the first time. To optimize the signal-to-noise ratio (SNR), the period having the greatest amplitude is chosen in step 52 for the further steps in the algorithm:

$$j \in \left[ j_{93} - \frac{3}{8}S ; \; j_{93}\frac{5}{8}S \right] \quad (21)$$

$j_{93}$ is about ⅛ period ahead of M5. To exactly determine the exact, i.e. interpolated position of the maximum M5 it is of no importance that the chosen period proceeds exactly from minimum to minimum.

However, in other embodiments also another ordinate value than 93% of the maximum can be chosen. Notably, this ordinate value may also be related to the minimum, the arithmetic mean of maximum and minimum, the difference between maximum and minimum and/or the constant component of the wave packet. If the ordinate value is smaller than the constant component of the wave packet, it is better to chose a first-time decrease below the ordinate value as reference point.

3. Now, the correlation coefficients $\phi_C$ and $\phi_S$ are calculated between $c_j$ and $W_j$ or $s_j$ respectively, and $W_j$ in steps 54 und 55, wherein $$c_j = \cos\left( \frac{2\pi f_{US} j}{f_S} \right) \quad (22)$$

$$s_j = \sin\left( \frac{2\pi f_{US} j}{f_S} \right) \quad (23)$$

Formulae (22) and (23) are calculated in steps 53 and 56. This may be done offline, so that the values are read, during the operation, from fields (lookup tables).

The calculation of the correlation coefficients corresponds from a mathematical point of view to the determination of a complex coefficient $\phi_C + i\phi_S$ of a discrete Fourier development:

$$y_j = (\varphi_C + i\varphi_S) \exp\left( i\frac{2\pi f_{US} j}{f_S} \right) \quad (24)$$

4. Instead of this complex representation one may indicate the absolute value and the phase $\phi$ of the oscillation, whereby the phase $\phi$ can be calculated by means of the arctan function, which is, however, one-valued only in an interval of length $\pi$. By taking into account the signs of $\phi_C$ and $\phi_S$, this interval may be extended to $2\pi$:

$$\phi = \arctan 2(\phi_S; \phi_C) \quad (25)$$

arc cot $2(\phi_C; \phi_S)$ is defined correspondingly.

Phase $\phi$ is calculated in step 57.

5. The propagation time is calculated from formula 26:

$$t = \left( j_{93} + \frac{1}{8} + \frac{\varphi}{2\pi} S \right) \frac{1}{f_S} \quad (26)$$

6. Analogously to the above-described TIDO algorithm it is, again, assumed in step 59 that $$j_M = \text{round}\left( j_{93,previous} + \frac{\varphi_{previous}}{2\pi} S \right)$$

is the point of the absolute maximum $M = W_{j_M}$, in order to bypass step 51 for reasons of calculation speed.

Like with the TiDO algorithm, a local maximum can be searched first, and adjacent local maximums can then be verified at an interval of in $\pm nS$ to find the global maximum, with n being an integer.

Both the TiDO and the TriTraX algorithms have the disadvantage that only one period of the entire ultrasound packet is evaluated, which results in a sub-optimal exactness of the determination of the propagation time.

WavTraX Algorithm

The Wavelet Transform by Cross (X) Correlation algorithm allows the use of a base adapted to the signal. The mother wavelet is chosen to correspond to an ultrasound packet as exactly as possible.

A non-linear fit applied to a typical ultrasound packet resulted in the mother sine and cosine wavelet for:

$$S_j = \sin\left( \frac{2\pi f_{US} j}{f_S} \right) \cdot \exp\left( -\left| \frac{j}{8,6 \cdot 10^{-6} s \cdot f_S} - 1{,}957 \right|^{3{,}24} \right), \quad (27)$$

wherein $0 \le j \le 10S$, $n \in N$ $$C_j = \cos\left( \frac{2\pi f_{US} j}{f_S} \right) \cdot \exp\left( -\left| \frac{j}{8,6 \cdot 10^{-6} s \cdot f_S} - 1{,}957 \right|^{3{,}24} \right), \quad (28)$$

wherein $0 \le j \le 10S$, $n \in N$

The mother wavelets are calculated in steps 61 and 62. The results can be stored in fields.

1. First, the position of the wave packet is determined with the aid of a cross-correlation function from the measured values $W_j$ with the mother sine wavelet in step 63.

$$K_{WS,\tau} = \sum_{j=0}^{10S} S_j W_{j+\tau} \quad (29)$$

The cross correlation function $K_{WS,T}$ reaches its maximum value if the position of the mother sine wavelet and the sampled ultrasound packet is in best possible coincidence. A maximum search in $K_{WS,T}$ provides point $T_M$ of the maximum of the cross correlation function. The maximum of the cross-correlation function is simultaneously the correlation factor $\phi_{WS}$ between the measured values and the mother sine wavelet:

$$\phi_{WS} = K_{WS,\tau M} \quad (30)$$

In this context it is already now pointed out that, in a more refined embodiment, an iteration can be incorporated into the maximum search, according to which, in equation (30), the beginning is at an optional T, i.e. not necessarily at $T_M$, but for example at $T_{M,previous}$, the $T_M$ of the preceding measurement. In step 66 then an improved estimate $T_B$ for $T_M$ is determined from equation (34). The result of this iteration is a local maximum. The maximum search in steps 72 to 80 is then limited to local maximums, the interval of which with respect to the maximum just determined substantially results from the frequency of the ultrasound.

2. The exact phase position of the wave packet is determined, similarly to the TriTraX algorithm, from the correlation factors between the measured values and the mother sine and cosine wavelet in step 65. This is equivalent to the determination of the phase position from the phase of a complex correlation factor. The correlation factor between the measured values and the mother sine wavelet is determined in step 64 from $$\varphi_{WC} = \sum_{j=0}^{10S} C_j W_{j+\tau_M} \quad (31)$$

3. The phase $\phi_W$ is determined from the correlation factors:

$$\phi_W = \text{arc cot } 2(\phi_{WC}; \phi_{WS}) \quad (32)$$

The propagation time results from:

$$t = \left(\tau_M + \frac{\varphi_W}{2\pi} S\right) \frac{1}{f_S} \quad (33)$$

If an estimate $T_S$ for the index $T_M$ of the maximum is already available, an improved estimate $T_B$ for the same measured values $W_j$ can be calculated from $$\tau_B = \tau_S + \frac{\varphi_W}{2\pi} \quad (34)$$

in step 66. $\phi_W$ results from equation (32), wherein $\phi_{WS}$ and $\phi_{WC}$ are calculated from equations (35) and (36) in steps 63 and 64.

$$\varphi_{WS} = \sum_{j=0}^{10S} S_j W_{j+\tau_S} \quad (35)$$

$$\varphi_{WC} = \sum_{j=0}^{10S} C_j W_{j+\tau_S} \quad (36)$$

$T_B$ does not necessarily indicate the phase position of the ultrasound packet exactly because the exponential function in the two mother wavelets represents an envelope for the sine and cosine components and distorts them. If the envelope of the received ultrasound packet (compare FIG. 5) does not yet coincide with the exponential component of the two mother wavelets because the interval from the global maximum $|T_S - T_M|$ is still too great, it cannot be expected that the improved estimate $T_B$ exactly indicates the phase position of the ultrasound packet. Insofar the amount of correlation factor $\phi_{WC}$ or $\phi_W$ in step 81 can be used as measure for the convergence.

According to equation (29) the maximum of the correlation factor $\phi_{WS}$ is determined by means of the mother sine wavelet (compare equation (30)). Due to the limited sampling rate, this maximum optimally deviates from the phase position of the ultrasound packet by up to $\pm 1/(2f_S)$. The factual deviations are slightly greater. The number of decimals of index $T_M$, which initially is an integer, are so to speak calculated by means of the mother cosine wavelet. As long as the mother cosine wavelet still provides for a displacement, the absolute value of which is greater than a threshold, it can be assumed that no sufficient convergence has been obtained yet. A sensible choice of this threshold is $1/f_S$. If S=16, the upper limit for $\phi_W$ amounts to $\pi/8$ or 22.5° and, thus, $$\phi_{WC}/\phi_{WS} > 0.414 \quad (37)$$

In the optimum case this upper limit for $\phi_W$ can be reduced to 11.25° and for $\phi_{WC}/\phi_{WS}$ to 0.199.

If this upper limit is exceeded and, therefore, another iteration step is to be performed, $T_B = T_M$ between the two iteration steps is rounded to an integer value in step 68. $T_M$ designated the interpolated index of the maximum of $\phi_{WC}$, to which $T_B$ converges. Alternatively, the measured values $W_j$ would have to be interpolated and the values of the function of both mother wavelets $S_j$ and $C_j$ would have to be calculated anew. Insofar $T_S$ in equation (34) is an integer, whereas $T_B$ typically comprises numbers of decimals.

In one embodiment, in which a microprocessor is used in which the calculation of the arc tangent function or the arc cotangent function is not implemented efficiently and therefore takes a long time, these functions can be calculated in step 65 with little exactness. A great exactness is required only when the condition in step 81 is fulfilled, that is, when the integer component of $T_B = T_M$ is known. In case of the prototype S=16, so that merely 4 thresholds have to be specified in a quadrant so as to determine the integer component of index $T_B$. This shows that the calculation of the arc tangent or arc cotangent function with the exactness required in step 65 can be implemented by means of a lookup table.

As was mentioned before, this iteration merely leads to a local maximum of $\phi_{WS}$, which is not necessarily equal to the global maximum of $\phi_{WS}$. Also, the interval of two local maximums is not always exactly equal to the period of the ultrasound because the exponential function distorts the sine and cosine function. Insofar the maximum search can be modified to perform alternately an iteration step according to equation (34) and a verification of the two adjacent local maximums. The two correlation coefficients $\phi_{WC}$ and $\phi_{WS}$ were calculated at point $T_S$. With round($T_B$) the correlation coefficients are only calculated in the next iteration step. The function round( ) rounds a floating point number to the next integer. As $T_S$ must initially merely ensure an overlap between the ultrasound packet and the wavelet, $\phi_{WS}$ may also be negative at the beginning of the iterations. Insofar it is appropriate to use the absolute value B($\tau$) for the maximum search, the calculation of which is exemplarily shown in step 67:

$$B(\tau) = \sqrt{\phi_{WS}^2 + \phi_{WC}^2} \quad (38)$$

However, an absolute value is also calculated in steps 73, 75, 77 and 79, even if this is accomplished at different points.

The number S, which may include a fractional component, indicates the number of measured values in an ultrasonic period. Therefore, the absolute values B(round($\tau_S \pm S$)) are to be calculated in steps 73 and 77 and be compared with absolute value B($\tau_S$). If B(round($\tau_S \pm S$))>B($\tau_S$), $\tau_{S+}$=round($\tau_B \pm S$) may be used as estimate according to steps 76 and 80, respectively, for the next iteration, in connection with step 68.

In another embodiment, if the absolute value B(round($\tau_S \pm S$)) is greater than the absolute value B($\tau_S$), further points round($\tau_S \pm nS$) in view of the absolute value B(round($\tau_S \pm nS$)) of the correlation factors can be examined in this direction in steps 75 and 79, respectively. These points are away from $T_S$ by an integer multiple of the period of the ultrasound. It is the goal of steps 75 and 76 to arrive at the global maximum already at the next iteration, if possible.

At a high measuring rate of the flow velocity, such subtleties are of less importance for the accelerations in the gas flow to be typically maximally expected in human respiration. Then, the phase positions of two ultrasound packets in two successive measurements differ to a small extent. Therefore, $T_M$ is already sufficiently close to $T_{M,previous}$, the point of the maximum in the preceding measurement, so that, when $T_{M,previous}$ is used as first estimate, merely one iteration step is necessary to determine $T_M$. In a case which is not quite so optimal, if the condition in step 81 is initially not fulfilled, two iterations are required, wherein the first iteration determines the integer component of $T_M$. After the exponential envelopes of the ultrasound packet and the two mother wavelets have been optimally brought into coincidence by the first iteration, the fractional component of the floating point number $T_M$ is exactly determined during the second iteration. A change from a local to a global maximum is then ideally not necessary, which can be verified in step 71.

To find out whether an estimate $T_S$ or an improved estimate $T_B$ is already in the correct ultrasonic period, the absolute value $B(\tau_S)$ can be compared in step 71 with a limit value $C_B$.

$$B(\tau_S) > C_B \tag{39}$$

This absolute value must be above the limit value $C_B$, which may depend on the flow velocity and, thus, on the propagation time difference $\Delta t$, but also on other parameters, such as the age of the ultrasonic transducers. Due to the intensity drop with high flows $C_B$ will decrease with a growing flow.

Another possibility to determine the correct period by using the WaveTraX algorithm consists in a combination with the TriTraX algorithm. Thus, the index $j_{93}$ can be determined first, the ordinate value $W_{j93}$ of which is closest to 0.93\*M. M is here the maximum of the measured data currently being evaluated (compare step 51). As estimate for the index $j_M$ of the maximum round($T_B$) may be used in step 59, wherein $T_B$ derives from the preceding measurement. After the determination of $j_{93}$ the first estimate $T_S$ can be calculated from $$\tau_S = j_{93} + \frac{S}{8} \tag{40}$$

The WaveTraX algorithm then proceeds in steps 63 and 64.

P-SEX Algorithm

Also the WaveTraX algorithm has proved to be only insufficiently robust, in particular if the signal amplitude and signal distortions are substantially reduced as a result of turbulences in case of high flows. Therefore, a new algorithm designated as P-SEX (Phase-Shifted Excitation and Cross Correlation (X)) was developed.

Figure 6:
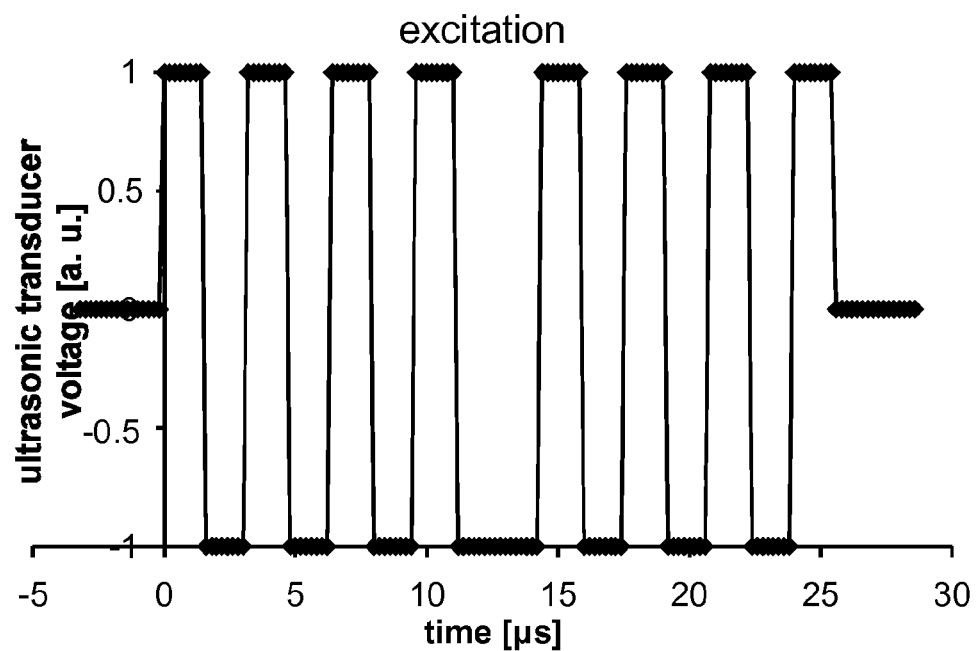
FIG. 6 shows the excitations when using the P-SEX algorithm.

The excitation of the ultrasonic transducers is accomplished by a square-wave voltage shown in FIG. 6, the phase of which is shifted by 180° or inverted after half of the excitation time, which is equivalent. The alternating voltage comprises a total of eight periods. The frequency of the alternating voltage $f_{us}$ is, again, 312.5 kHz and thus corresponds to approximately the resonance frequency of the ultrasonic transducers.

Figure 7:
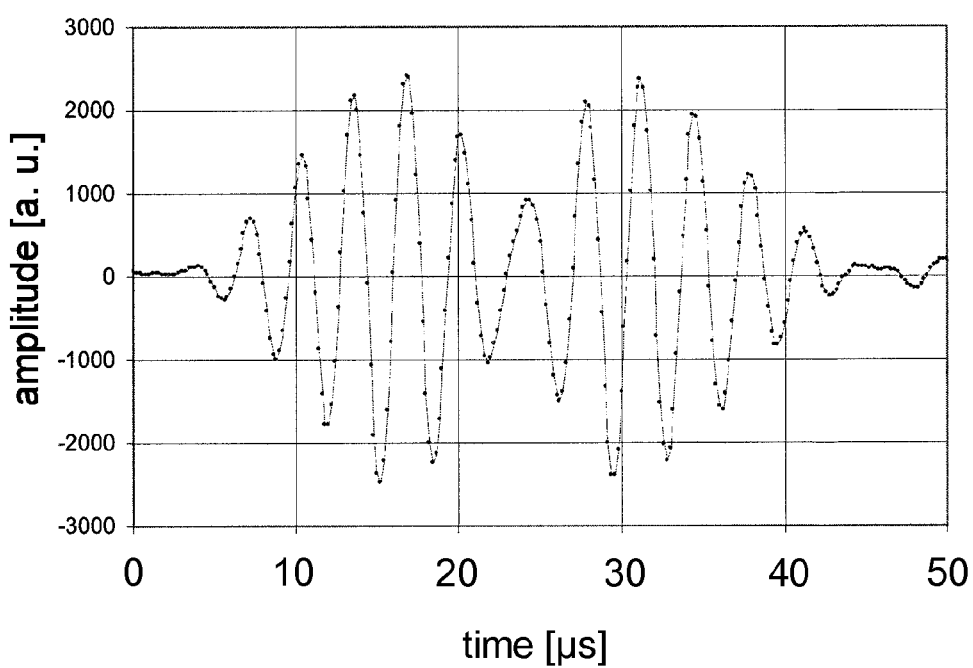
FIG. 7 shows a typical, received ultrasound packet when using the P-SEX algorithm.

The signal received when the medium is at rest, which is shown by way of example in FIG. 7, likewise shows a phase jump. One can conceive the received signal as two halves that are phase-shifted to each other. If the signal deteriorates at higher flows, the transition range of the phase is no longer well-defined.

Figure 8:
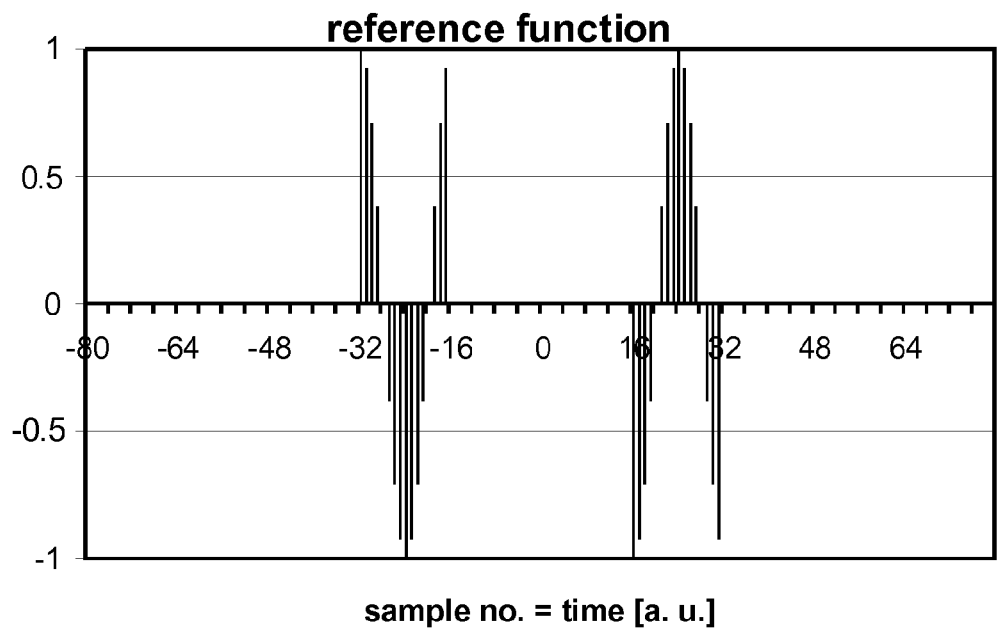
FIG. 8 shows a reference function when using the P-SEX algorithm.
Figure 9:
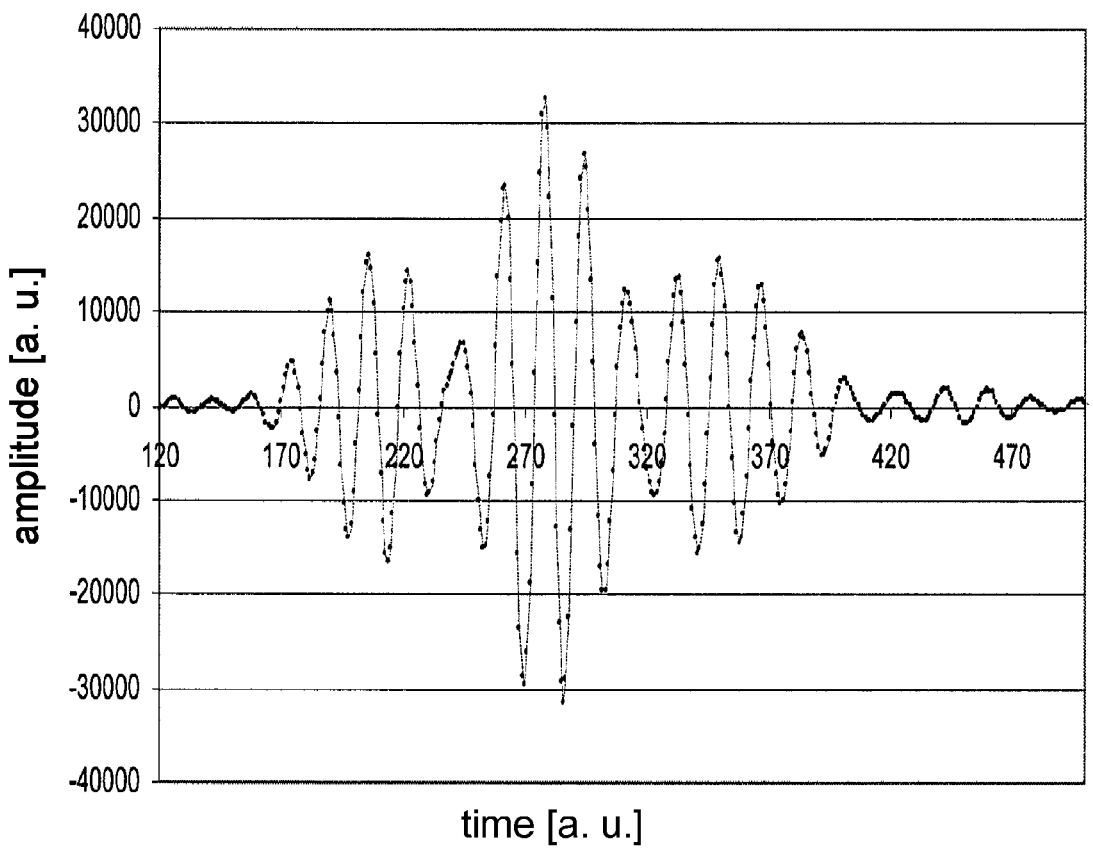
FIG. 9 shows a cross-correlation function between an ultrasound packet and a reference function when using the P-SEX algorithm.

1. Therefore, unlike the WaveTraX algorithm, not a function resembling the received signal is used as reference function for the calculation of a cross-correlation function, but the reference function illustrated in FIG. 8 is rather used, in which the transition range is "cut out". It was found by means of simulations that a reference function as illustrated in FIG. 8 with one period cos, 2 periods zero, one period cos provides a cross-correlation function as illustrated in FIG. 9 with the received signal, in which the global maximum is above the next lower maximum by approximately 23%. By this, the P-SEX algorithm no longer jumps so easily to an incorrect maximum. With the excitation of 5 periods used in the TiDO, TriTraX and WaveTrax algorithms, which results in a typical signal shape of the received signal as illustrated in FIG. 5, the difference is just about 1%.

2. It is even better to look at the left one of the two minimums with the largest absolute values, which will be referred to as left minimum $T_{IM}$ below. The difference over the minimum with the next smaller absolute value is nearly 50% in contrast to the 23% of the maximum.

It was observed, however, that the minimum left of the left minimum becomes very large in terms of its absolute value, especially larger than the absolute value of the minimum (which is global when the flows are small) right of the left minimum $T_{IM}$. At the same time, the form of the P-SEX cross-correlation function, which is changed if flows are high, results in that the left minimum $T_{IM}$ grows, in terms of its absolute value, to the global minimum and is well-defined (FIG. 9).

Thus, in the cross-correlation function KKF according to equation (41) the global minimum $y_1$ is searched for at point T. Then, the two adjacent minimums $y_0$ and $y_2$ according to equations (42) and (43) are examined at points T–S and T+S. If the flows are small, $y_0$ is the left minimum. If the flows are high, $y_1$ is the left minimum grown to the global minimum and $y_2$ is the global minimum if the flows are small. The choice of the left minimum $T_{IM}$ is accomplished in equation (44).

$$y_1 = \operatorname{Min}(KKF) = KKF(\tau) \tag{41}$$

$$y_0 = KKF(\tau - S) \tag{42}$$

$$y_2 = KKF(\tau + S) \tag{43}$$

$$\tau_{IM} = \begin{cases} \tau - S & \text{if } y_0 < y_2 \\ \tau & \text{otherwise} \end{cases} \tag{44}$$

As a result, this algorithm searches in principle for the left minimum. The propagation time difference, as of which the left minimum has grown to the global minimum, is approximately 5 μs. As compared to this, the propagation time difference with a maximum flow of 20 l/s amounts, on the basis of the current dimensioning of the tube cross-section, to approximately 24 μs. Thus, the rough position of the sound packet can be well determined.

3. For the exact phase determination the cos-period $(-\pi \ldots \pi)$, which follows the searched minimum, is chosen in the cross-correlation function:

$$W_i = KKF(\tau_M + i), i=0, 1, 2, \ldots, S \tag{45}$$

4. The $W_i$ are developed analogously to steps 54 and 55 of the TriTraX algorithm according to a cosine or sine function, respectively, wherein the coefficients $\phi_C$ and $\phi_S$ are calculated.

Figure 1:
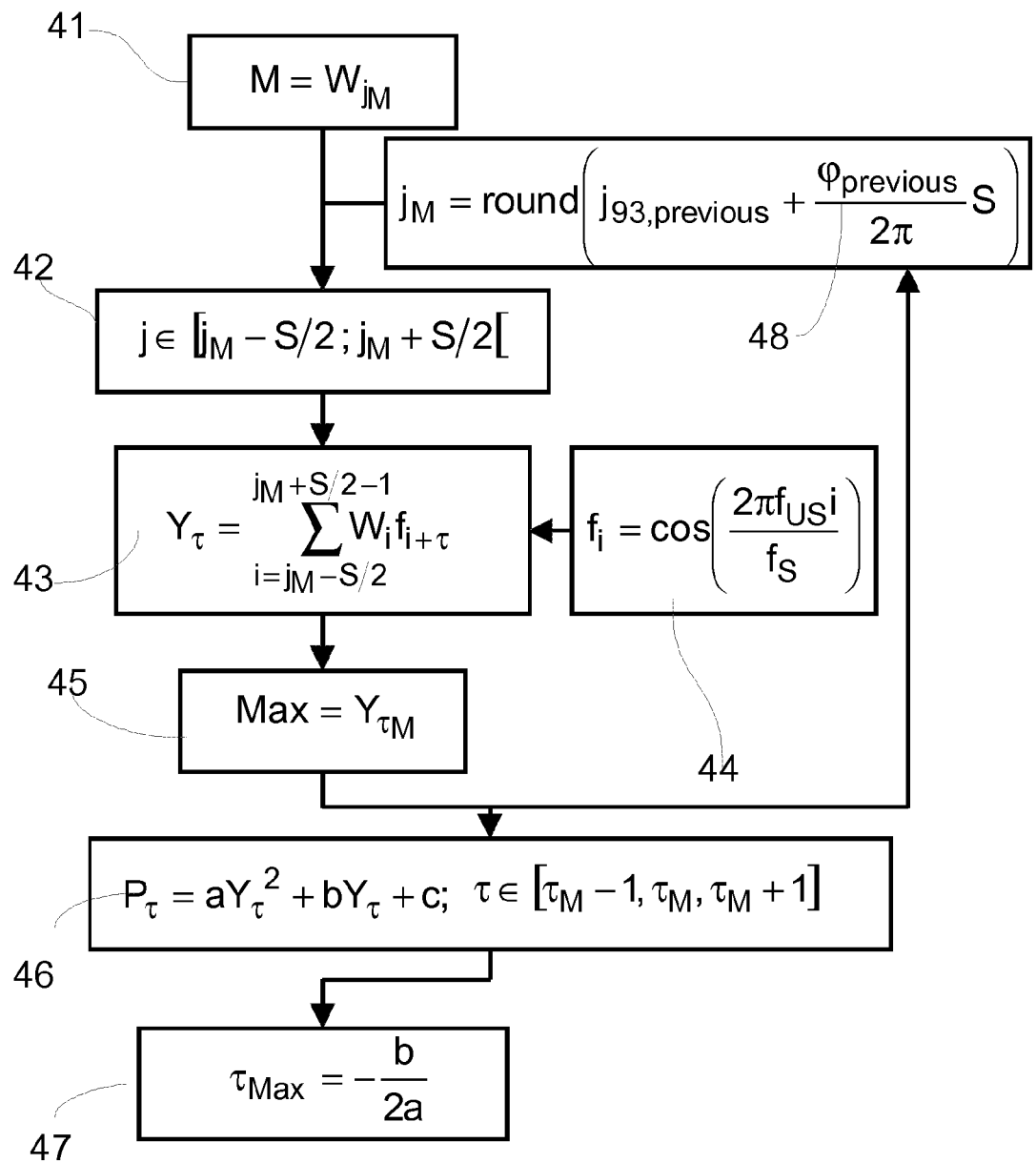
FIG. 1 shows a flowchart of a TiDO algorithm.
Figure 2:
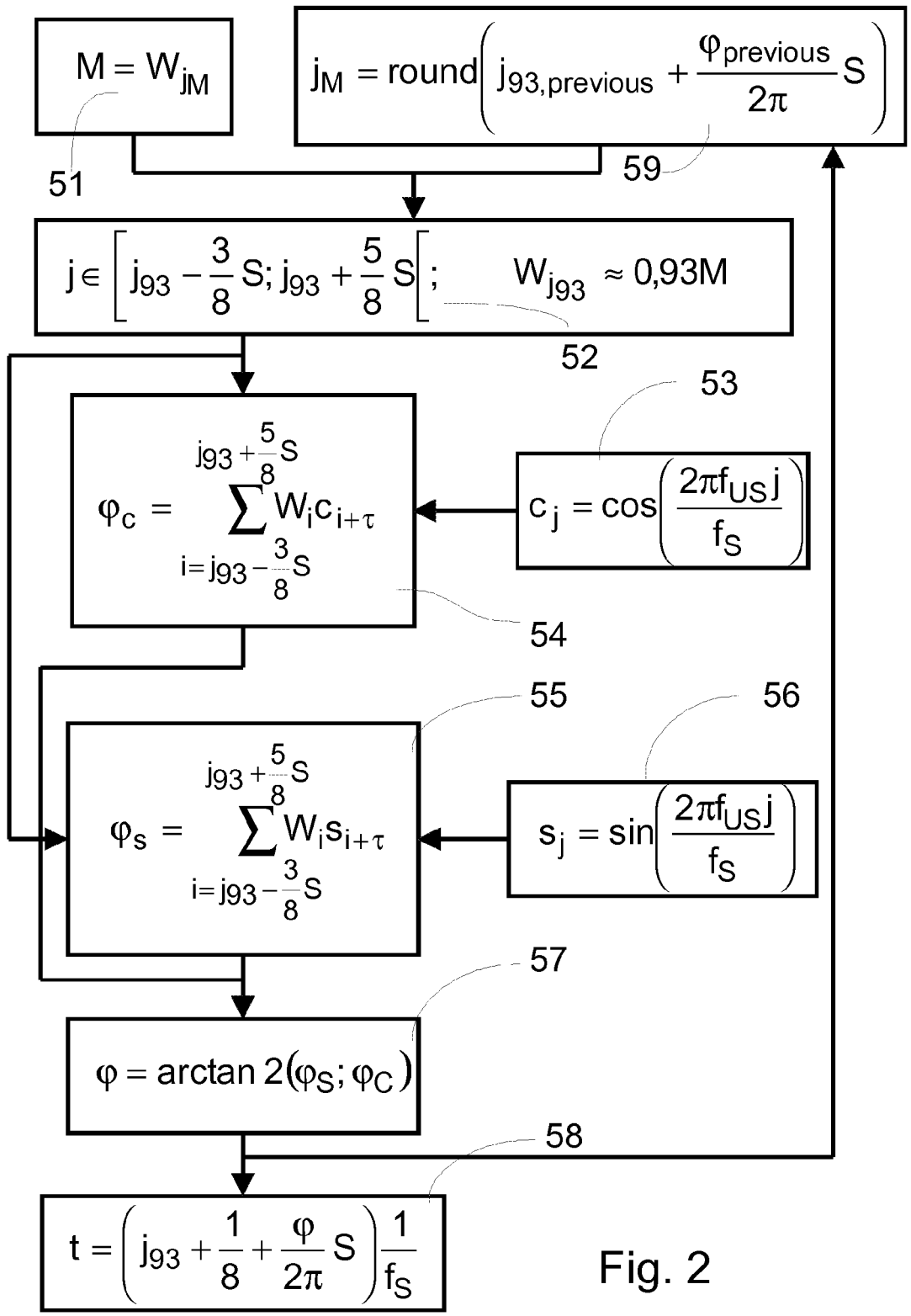
FIG. 2 shows a flowchart of a TriTraX algorithm.

5. Next, in correspondence with step 57 in FIG. 2 and equation (25), the phase $\phi$ is calculated by means of an arctan 2-function. This results in a phase determination with a smaller error, in contrast to allowing for a period out of the signal or fitting the maximum of the cross-correlation function by a parabola.

6. Finally, the propagation time t is calculated from equation (46):

$$t = \tau_M + \frac{\varphi}{2\pi f_{US}} \quad (46)$$

Further modifications in addition to the above-described algorithms are possible. Especially, the received ultrasonic signal can be correlated or convoluted with a reference function representing the inverse of the transmission path. Depending on the definition of the transmission path, e.g. power amplifier-ultrasonic transducer-air-ultrasonic transducer or trigger pulse-square-wave generator-power amplifier-ultrasonic transducer-air-ultrasonic transducer, the result of the convolution or correlation can be, for example, a pulse or a square alternating voltage. Particularly advantageous are correlation functions which convert the received ultrasonic signal by approximation into a Dirac delta function, whereby ideally only the value of a time interval differs considerably from zero.

For determining the correct interval another correlation function can be used compared to that for determining the phase.

Figure 10:
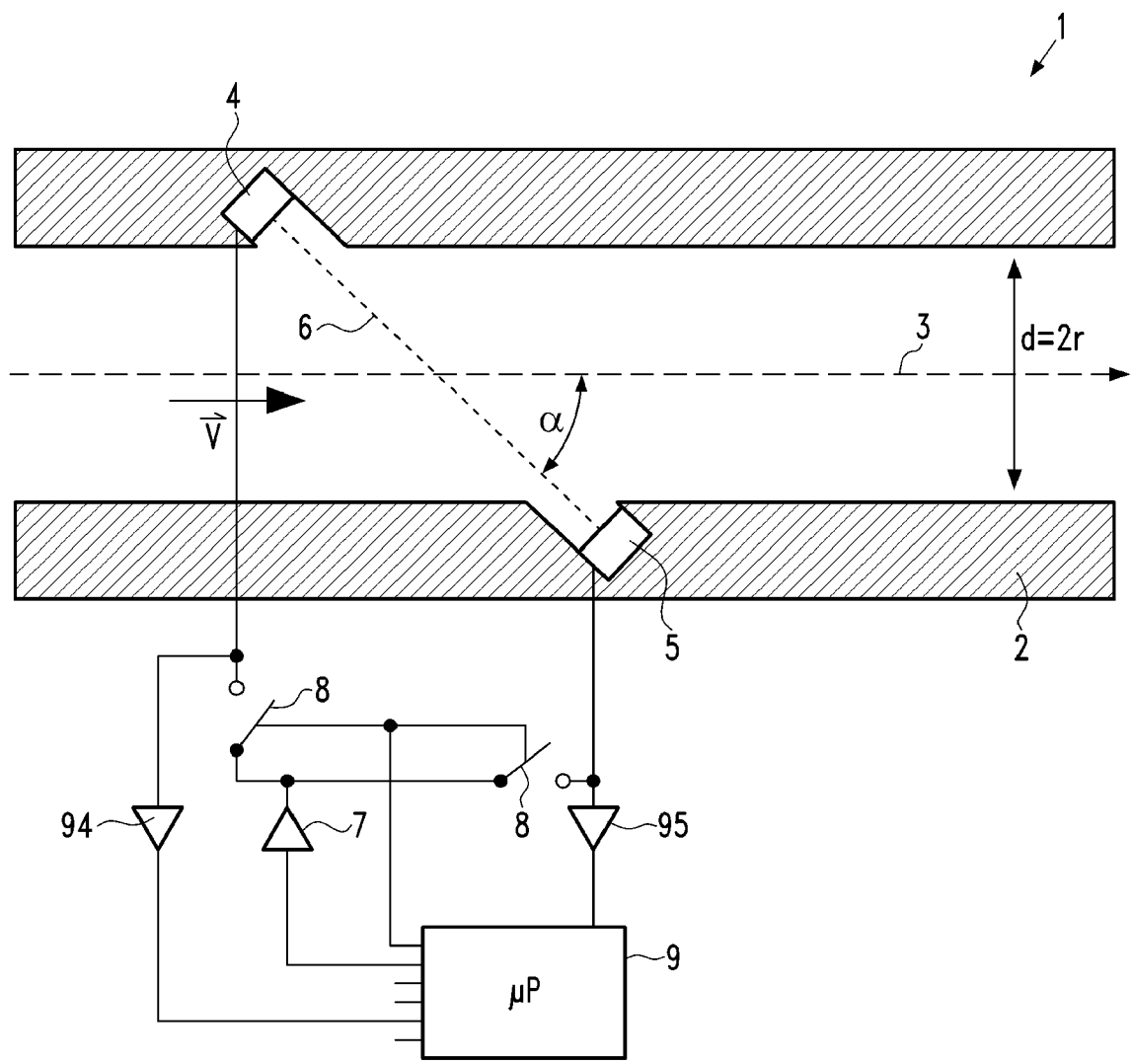
FIG. 10 shows a construction type of a known spirometer including a wiring according to the invention.
Figure 11:
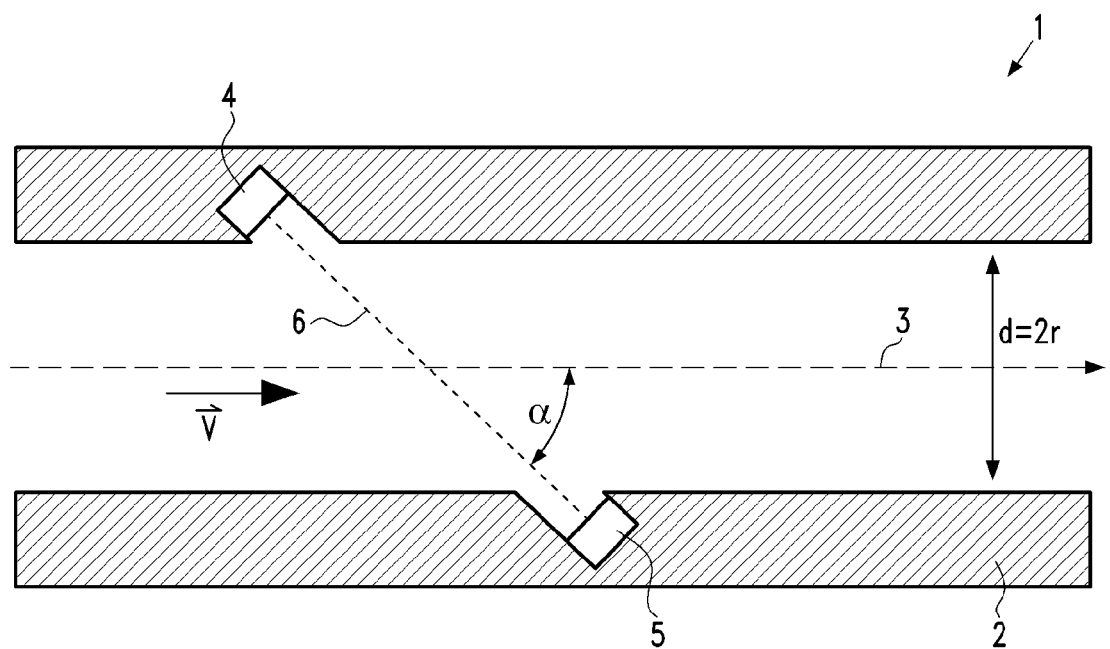
FIG. 11 shows a construction type of a known spirometer.
Figure 12:
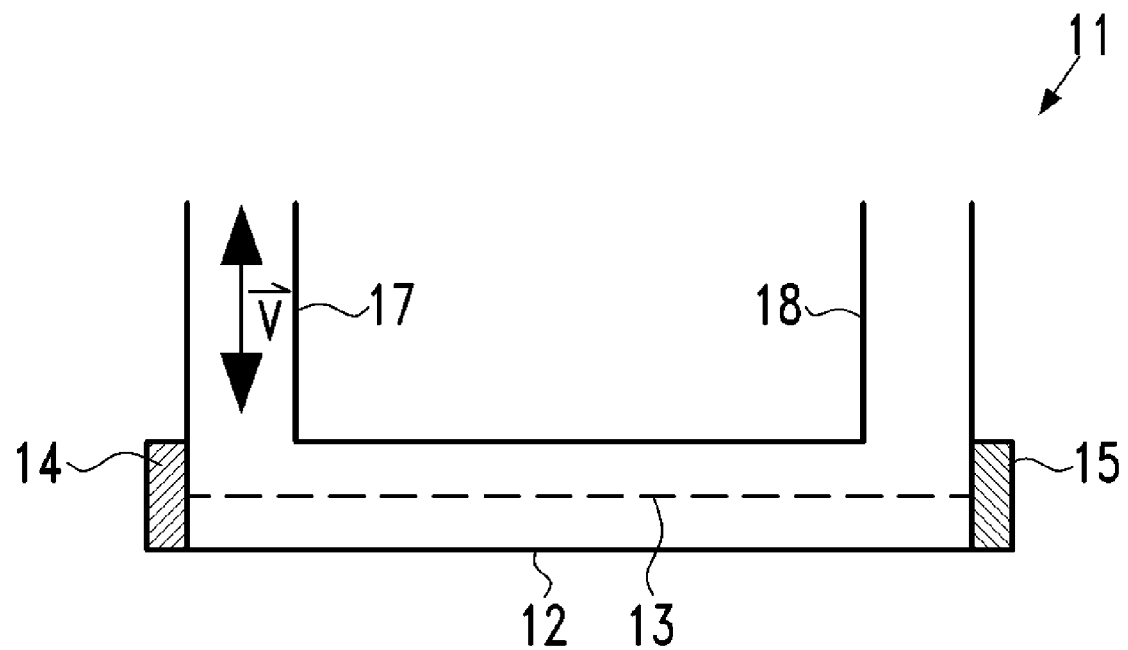
FIG. 12 shows another construction type of a known spirometer.

FIG. 10 shows a construction type of a known spirometer from FIG. 11, comprising a wiring according to the invention. The core of the controller is the microprocessor 9. Particularly a digital signal processor may be used as microprocessor, which is able to perform the calculation of sum products particularly fast. Such sum products appear, for example, in equations (16), (29), (31), (35) and (36). The microprocessor 9 controls particularly the driver circuit 7, which generates the alternating voltage for the two ultrasonic transducer 4 and 5. As both transducers are to transmit at the same time, merely one driver circuit is necessary.

Figure 3:
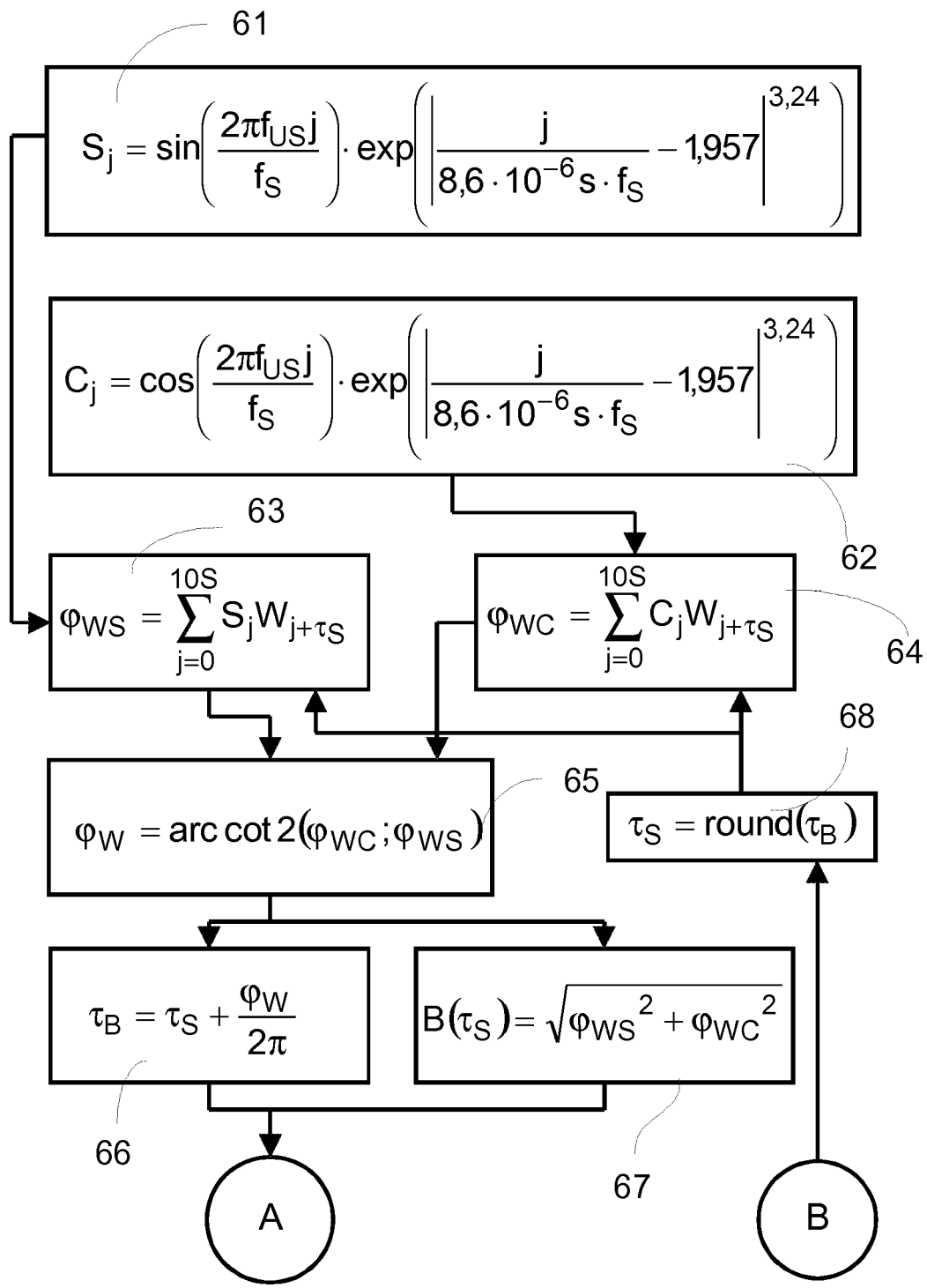
FIG. 3 shows a flowchart of a part of a WaveTraX algorithm.
Figure 4:
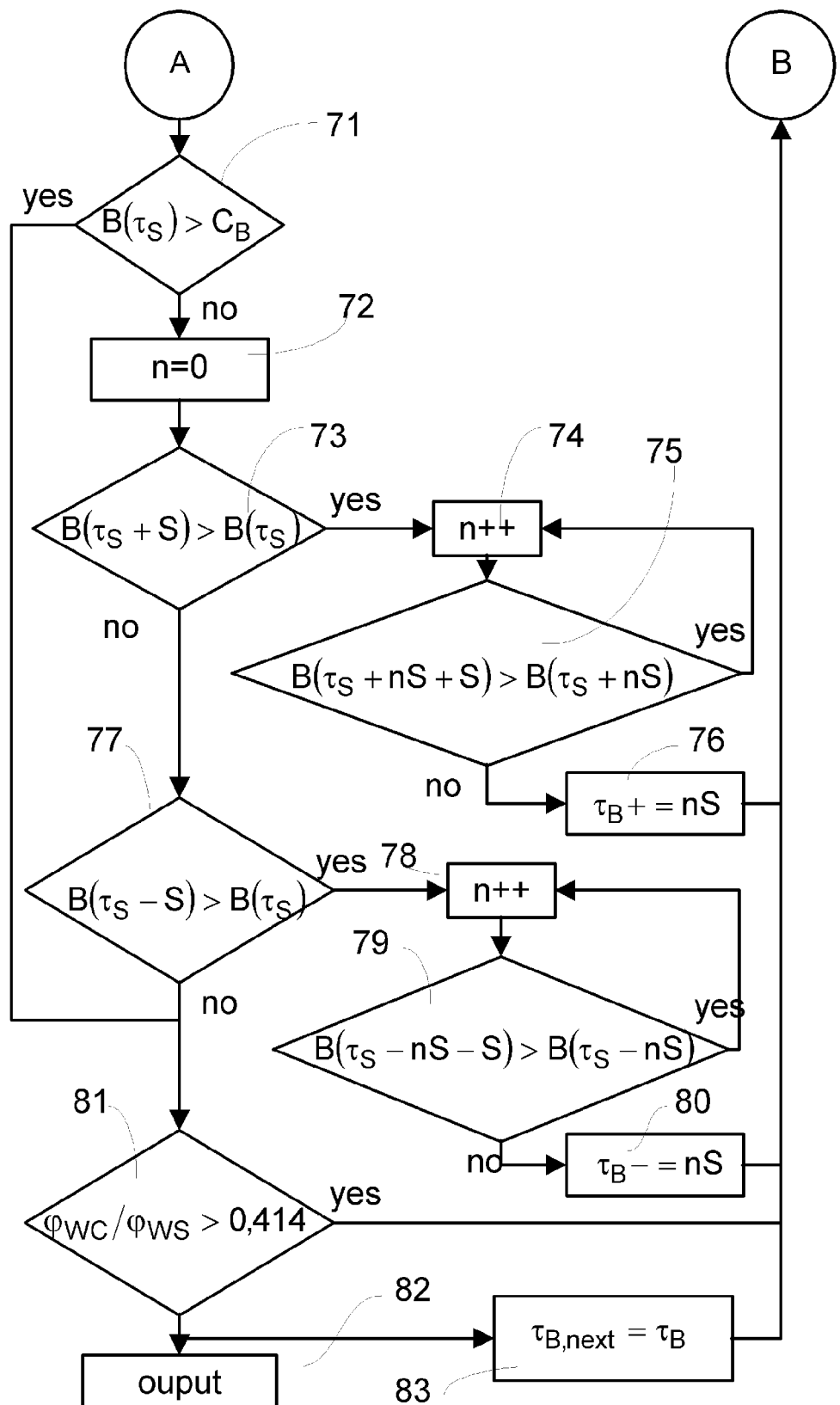
FIG. 4 shows a flowchart of a second part of the WaveTraX algorithm.

Especially during the receive operation must the transducers be separated from the driver circuit, which can be done, for example, by the switches 8 which are actively switched on and off by the microprocessor 9. This separation can also be accomplished by switching the output of the driver circuit 7 into a high impedance condition. A third possibility is the use of nonlinear components such as diodes, as is disclosed, for example, in EP 0 234 515 A1, FIG. 3.

In the receive operation the electric signals provided by the ultrasonic transducers are digitalized by the analog-digital converters 94 and 95 and are supplied to the microprocessor 9 for the further processing thereof. In one prototype DSPs of the TMS320C24x series (Texas Instruments) were employed, which comprise a 12 bit ADC and a 32 bit CPU.

Especially the tube 2 is not regarded as a component essential for the invention because the tube itself, or at least an insertion tube, is embodied to be interchangeable to allow a better disinfection thereof, which is why it is sold separately from the spirometer. Moreover, the mean flow velocity in the direction of the axis 6 defined by the transducers 4 and 5 may be a sensible measurement signal for an anemometer, without a surface being specified so that, consequently, no flow rate can be determined.

Although the position of the transmitted ultrasound packets is easily determinable because the microprocessor 9 triggers the driver circuit 7, it should be emphasized that the technical problem resides in the exact determination of the propagation time difference $\Delta t$, not so much the propagation times $t_{45}$ and $t_{54}$ or the mean propagation time $t_0$.

Because of the meanwhile available ultrasonic transducers short ultrasonic pulses can be generated. Thus, the duration of the ultrasound packet illustrated in FIG. 5 is 20 to 30 µs. The fading behavior after an ultrasonic pulse is so good that the same ultrasonic transducer can be used for receiving an ultrasound packet after the propagation time of an ultrasound packet of approximately 160 µs has lapsed after emitting an ultrasonic pulse. Therefore, in one embodiment, both ultrasonic transducers 4 and 5 or 14 and 15 emit ultrasonic pulses simultaneously, which are received again by both ultrasonic transducers approximately 160 µs later. Thus, the measuring points $W_j$ are already available after 160 µs for a propagation time measurement in both directions, so that the propagation time difference $\Delta t$ and the mean propagation time $t_0$ can already be calculated from these measured data.

If there is sufficient memory space and computing power, the two next ultrasound packets can be sent immediately after two first ultrasonic packets were registered. During the propagation time of the next ultrasound packets the evaluation of the registration of the first ultrasound packets can be performed. The flow rate, which is calculated from the two first ultrasound packets, can then be available shortly before the next two ultrasound packets are registered. Thus, the above-indicated sampling rates of 6.25 kHz for the measurement of the velocity can be reached.

In any of the above-described embodiments the difference of the velocity determined in two successive measurements can be evaluated as plausibility check, the amount of which has to be smaller than a maximum change rate of the velocity multiplied by the time interval of the two measurements. If this is not the case, an error report can be outputted and/or the younger measured value can be discarded.

Although the preferred embodiment was described above in connection with air, the invention can be used with any other fluid to determine a flow velocity or flow rate.

The invention was explained in more detail by means of preferred embodiments above. A person skilled in the art will appreciate, however, that various alterations and modifications may be made without departing from the gist of the invention. Therefore, the scope of protection will be defined by the appended claims and their equivalents.

Mathematical Symbols:
α: angle between axes 3 and 6
c: sound velocity in medium at rest
$C_B$, $C_1$, $C_2$: constants
$S_j$, $C_j$: "samples" of the mother sine and cosine wavelets
$f_{US}$: ultrasonic frequency
$f_S$: sampling rate
f(t), g(t): time-dependent functions
j: index of measured values
$j_M$: index of M
L: distance of ultrasonic transducers
M: maximum of $W_j$
$\phi_C$, $\phi_S$: correlation coefficients
$\phi_{WS}$, $\phi_{WC}$: correlation coefficients
$\phi_W$: phase
$\Delta t$: propagation time difference
$t_0$: mean propagation time
$t_{45}$, $t_{54}$ sound propagation times
φ: cross-correlation function
r: radius of tube 2
S: $f_S/f_{US}$ (in one embodiment 16)
v: flow velocity of the medium
$\dot{V}$: flow rate
$W_j$ measured values
$Y_T$: time-discrete cyclic variant
$T_M$: (interpolated) index
$T_S$: (integer) estimate for $T_M$
$T_B$: improved estimate for $T_M$

LIST OF REFERENCE NUMBERS 1, 11 flow measuring apparatus
2 tube
3 axis
4, 5, 14, 25 ultrasonic transducers
6 axis
7 driver circuit
8 switch
9 microprocessor
94, 95 analog-digital converter
12 horizontal leg
13 axis
17, 18 vertical leg
31 sound packet
M1, M2, M3, M4, M5, M6, M7, M8 maximums
41-83 steps

What is claimed is:

1. Method for determining the temporal position of a wave packet (31) in a flow measuring apparatus, in particular a spirometer, comprising:
providing at least one transducer for sampling (94, 95) the wave packet at a plurality of points in time, wherein a measured value is created at each point in time;
providing a microprocessor for calculating a sum of products (43, 54, 55, 63, 64), wherein each product is calculated for a determined point in time from the plurality of points in time and each product is the product of a value of a compare function (44, 53, 56, 61, 62) at said determined point in time and the measured value at said determined point in time; and
calculating (46, 47, 57, 58, 65-81) the temporal position of the wave packet from the sum of products,
wherein the compare function is a sine function (56) from which a second sum of second products is calculated (54), wherein each second product is calculated for another determined point in time from the plurality of points in time and each second product is the product of a value of a cosine function (53) at said another determined point in time and the measured value at said determined point in time, and the temporal position of the wave packet is calculated as arc tangent function (57) of the quotient from the sum of products divided by the second sum of second products.

2. Method for determining the temporal position of a wave packet (31) in a flow measuring apparatus, in particular a spirometer, comprising:
providing at least one transducer for sampling (94, 95) the wave packet at a plurality of points in time, wherein a measured value is created at each point in time;
providing a microprocessor for calculating a sum of products (43, 54, 55, 63, 64), wherein each product is calculated for a determined point in time from the plurality of points in time and each product is the product of a value of a compare function (44, 53, 56, 61, 62) at said determined point in time and the measured value at said determined point in time; and
calculating (46, 47, 57, 58, 65-81) the temporal position of the wave packet from the sum of products,
wherein the compare function is a sine function multiplied by an exponential function (61), wherein the argument of the exponential function results from a power of a first value weighted by a factor, said first value being the absolute value of the difference of the point in time minus a temporal offset.

3. Method according to claim 2, characterized in that a second sum of second products is calculated, wherein each second product is calculated for another determined point in time from the plurality of points in time and each second product being the product of a value of a second compare function at another determined point in time and the measured value at said determined point in time, wherein the second compare function is a cosine function multiplied by an exponential function (62), wherein the argument of the exponential function results from the power of a second value weighted by the factor, said second value being the absolute value of the difference of said another determined point in time minus the temporal offset, and that the temporal position of the wave packet is calculated as arc cotangent function (65) of the quotient from the second sum of second products divided by the sum of products.

4. Method according to claim 3, characterized by:
shifting the compare function and the second compare function (68) by the time interval between two measured values, so that the compare function coincides as good as possible with the temporal position of the wave packet calculated from the arc cotangent function;
newly calculating (63, 64) the sum of products with the shifted compare function and the second sum of products with the shifted second compare function; and
calculating a better estimate for the temporal position of the wave packet as arc cotangent function (65) of the quotient from the newly calculated second sum of second products divided by the sum of products.

5. Method according to claims 3 or 4, characterized by:
shifting (73, 75, 77, 79) the compare function by the time interval between two measured values, which corresponds approximately to an integer multiple of a period of the wave packet, wherein the compare function was already shifted once so as to bring its position into coincidence with the temporal position of the wave packet;
calculating the sum of products with the shifted compare function;
repeating the shifting and calculating so as to obtain a plurality of sums of products; and
choosing the temporal offset of the compare function at which the sum of products becomes maximal.

6. Method according to claim 5, characterized in that a geometrical sum (67) of the sum and the second sum is calculated and the geometrical sum is maximized (73, 75, 77, 79) so as to choose the correct period of the wave packet.

7. Method according to claim 6, characterized by:
determining the measuring point at which the wave packet exceeds for the first time a predetermined fraction of the maximum of all measuring points of the wave packet;
choosing (52) a period of the wave packet around the determined measuring point so as to calculate the sums of products.

8. Method according to claim 5, characterized by:
determining the measuring point at which the wave packet drops for the first time below a predetermined fraction of the minimum of all measuring points of the wave packet;
choosing a period of the wave packet around the determined measuring point so as to calculate the sums of products.

9. Method according to claims 1 or 2, characterized by:
calculating (43) a plurality of sums of products, wherein different compare functions, but the same measured values are used, wherein the compare functions are each shifted by a different time difference, but are equal otherwise;
determining (45) the maximum of the sums of products; and calculating the temporal position of the wave packet from the time difference by which the compare function was shifted, which was used to calculate the maximum sum of products.

10. Method according to claim 9, characterized by:
laying (46) a parabola through the maximum sum of products and the two adjacent sums which are calculated from compare functions, which are shifted forward and backward by the time interval of two adjacent measuring points with respect to the compare function of the maximum sum; and
calculating (47) the temporal position of the wave packet from the position of the vertex of the parabola.

11. Method according to claims 1 or 2, characterized in that the at least one transducer generating the wave packet is driven by an AC signal having a phase jump.

12. Method according to claim 11, characterized in that the compare function consists of a cosine period, two periods zero, an inverse cosine period and otherwise zero.

13. Flow measuring apparatus (1, 11), comprising:
a first sonic transducer (4, 14);
a second sonic transducer (5, 15), wherein the two sonic transducers are aligned with respect to each other so that the second sonic transducer (5, 15) absorbs a part of the sound generated by the first sonic transducer (4, 14) and vice versa, wherein the two sonic transducers convert an electric signal to sound and vice versa;
a driver circuit (7) which is connected to the first sonic transducer (4, 5, 14, 15) and temporarily supplies the first sonic transducer with an alternating voltage to generate sound;
characterized by: an analog-digital converter (94, 95) for sampling and digitalizing the electric signal emitted by the second sonic transducer at a plurality of points in time, wherein a measured value is created at each point in time, wherein the input of the analog-digital converter (94, 95) is connected to the second sonic transducer (4, 5, 14, 15), a microprocessor (9) connected to the output of the analog-digital converter (94, 95) and to which the measured values are supplied, said microprocessor (9) performing the following steps:
calculating a sum of products (43, 54, 55, 63, 64), wherein each product is calculated for a determined point in time from the plurality of points in time and each product is the product of a value of a compare function (44, 53, 56, 61, 62) at said determined point in time and the measured value at said determined point in time; and
calculating (46, 47, 57, 58, 65-81) the temporal position of the wave packet from the sum of products, wherein
the compare function is a sine function (56, 61), from which the microprocessor (9) calculates (54, 64) a second sum of second products, wherein each second product is calculated for another determined point in time from the plurality of points in time and each second product is the product of a value of a cosine function (53, 62) at said another determined point in time and the measured value at said determined point in time, and calculates the temporal position of the wave packet as arc tangent function (57, 56) of the quotient from the sum of products divided by the second sum of second products.

14. Flow measuring apparatus (1, 11), comprising:
a first sonic transducer (4, 14);
a second sonic transducer (5, 15), wherein the two sonic transducers are aligned with respect to each other so that the second sonic transducer (5, 15) absorbs a part of the sound generated by the first sonic transducer (4, 14) and vice versa, wherein the two sonic transducers convert an electric signal to sound and vice versa;
a driver circuit (7) which is connected to the first sonic transducer (4, 5, 14, 15) and temporarily supplies the first sonic transducer with an alternating voltage to generate sound;
characterized by: an analog-digital converter (94, 95) for sampling and digitalizing the electric signal emitted by the second sonic transducer at a plurality of points in time, wherein a measured value is created at each point in time, wherein the input of the analog-digital converter (94, 95) is connected to the second sonic transducer (4, 5, 14, 15), a microprocessor (9) connected to the output of the analog-digital converter (94, 95) and to which the measured values are supplied, said microprocessor (9) performing the following steps:
calculating a sum of products (43, 54, 55, 63, 64), wherein each product is calculated for a determined point in time from the plurality of points in time and each product is the product of a value of a compare function (44, 53, 56, 61, 62) at said determined point in time and the measured value at said determined point in time; and
calculating (46, 47, 57, 58, 65-81) the temporal position of the wave packet from the sum of products, characterized in that the compare function is a sine function multiplied by an exponential function (61), wherein the argument of the exponential function results from a power of a first value weighted by a factor, said first value being the absolute value of the difference of the point in time minus a temporal offset.

15. Flow measuring apparatus according to claim 14, characterized in that the microprocessor (9) calculates a second sum of second products, wherein each second product is calculated for another determined point in time from the plurality of points in time and each second product is the product of a value of a second compare function at said another determined point in time and the measured value at said determined point in time, wherein the second compare function is a cosine function multiplied by an exponential function (62), wherein the argument of the exponential function results from the power of a second value weighted by the factor, said second value being the absolute value of the difference of said another determined point in time minus the temporal offset and that the temporal position of the wave packet is calculated as arc tangent function (65) of the quotient from the sum of products divided by the second sum of second products.

16. Flow measuring apparatus according to claim 15, characterized in that the microprocessor (9) further performs the following steps:
shifting the compare function and the second compare function (68) by the time interval between two measured values, so that the compare function coincides as good as possible with the temporal position of the wave packet calculated from the arc cotangent function;
newly calculating (63, 64) the sum of products with the shifted compare function and the second sum of products with the shifted second compare function; and
calculating a better estimate for the temporal position of the wave packet as arc tangent function (65) of the quotient from the newly calculated sum of products divided by the second sum of second products.

17. Flow measuring apparatus according to claims 15 or 16, characterized in that the microprocessor (9) further performs the following steps:
shifting (73, 75, 77, 79) the compare function by the time interval between two measured values which corresponds approximately to an integer multiple of a period of the wave packet, wherein the compare function was already shifted once so as to bring its position into coincidence with the temporal position of the wave packet;

calculating the sum of products with the shifted compare function;

repeating the shifting and calculating defined in this claim so as to obtain a plurality of sums of products; and choosing the temporal offset of the compare function at which the sum of products becomes maximal.

18. Flow measuring apparatus according to claim 17, characterized in that the microprocessor (9) calculates a geometrical sum (67) of the sum and the second sum and maximizes (73, 75, 77, 79) the geometrical sum so as to choose the correct period of the wave packet.

19. Flow measuring apparatus according to claim 18, characterized in that the microprocessor (9) further performs the following steps:

determining the measuring point at which the wave packet exceeds for the first time a predetermined fraction of the maximum of all measuring points of the wave packet;

choosing (52) a period of the wave packet around the determined measuring point so as to calculate the sums of products.

20. Flow measuring apparatus according to claim 18, characterized in that the microprocessor (9) further performs the following steps:

determining the measuring point at which the wave packet drops for the first time below a predetermined fraction of the minimum of all measuring points of the wave packet;

choosing a period of the wave packet around the determined measuring point so as to calculate the sums of products.

21. Flow measuring apparatus according to claims 13 or 14, characterized in that the microprocessor (9) further performs the following steps:

calculating (43) a plurality of sums of products, wherein different compare functions, but the same measured values are used, wherein the compare functions are each shifted by a different time difference, but are equal otherwise;

determining (45) the maximum of the sums of products; and calculating the temporal position of the wave packet from the time difference by which the compare function was shifted, which was used to calculate the maximum sum of products.

22. Flow measuring apparatus according to claim 21, characterized in that the microprocessor (9) further performs the following steps:

laying (46) a parabola through the maximum sum of products and the two adjacent sums which are calculated from compare functions, which are shifted forward and backward by the time interval of two adjacent measuring points with respect to the compare function of the maximum sum; and calculating (47) the temporal position of the wave packet from the position of the vertex of the parabola.

\* \* \* \* \*